United States Patent [19]

Sieg

[11] Patent Number: 5,363,973

[45] Date of Patent: Nov. 15, 1994

[54] TEST SAMPLE CHANGER

[76] Inventor: Christopher Sieg, 96 W. Main St., Hillsborough, N.H. 03244

[21] Appl. No.: 175,746

[22] Filed: Dec. 30, 1993

Related U.S. Application Data

[62] Division of Ser. No. 704,088, May 22, 1991, Pat. No. 5,297,922.

[51] Int. Cl.⁵ .............................................. A47F 5/00
[52] U.S. Cl. ...................................... 211/41; 211/163
[58] Field of Search ...................... 211/41, 40, 163, 4; 221/76, 242; 206/455; 312/9.31

[56] References Cited

U.S. PATENT DOCUMENTS

| | | | |
|---|---|---|---|
| 1,372,100 | 3/1921 | Siffert | 211/163 X |
| 3,161,294 | 12/1964 | Meuche | 211/41 |
| 3,764,040 | 10/1973 | Solomon | 221/76 |
| 4,014,437 | 3/1977 | Rumble et al. | 211/4 |
| 5,176,264 | 1/1993 | De Polma | 211/41 |

*Primary Examiner*—Alvin C. Chin-Shue
*Assistant Examiner*—Sarah A. Lechok
*Attorney, Agent, or Firm*—Stephen G. Matzuk

[57] ABSTRACT

A sample changer for precise positioning of a selected sample from a plurality of samples stored on a removable annular sample file. The samples comprising a rectangular dimensioned object is radially removed from the annular cassette and precisely positioned at a predetermined location for testing. Upon completion of the desired testing, the sample is replaced into the cassette which is repositioned and a subsequently selected sample is accordingly extracted and positioned for testing. Furthermore, the present invention includes a combination of elements which act together to detect and dislodge samples which may become temporarily stuck or jammed in the mechanism, reducing the need for operator intervention. Furthermore, the annular cassette is removable from the sample changing mechanism and includes a concentric locking ring which selectively retains all samples within the cassette or permits the removal of all samples. The sample changer mechanism includes a stationary arcuate slide retainer wherein the slides released by the annular locking ring are retained within the cassette mechanism until selectively positioned and lowered into the mechanism for testing.

4 Claims, 5 Drawing Sheets

TEST SAMPLE CHANGER

This application is a division of application Ser. No. 07/704,088, filed May 22, 1991, now U.S. Pat. No. 5,297,922.

FIELD OF THE INVENTION

The present invention relates to sample changing apparatus, in particular to apparatus for selectively removing one sample from a plurality of samples stored in a cassette and positioning the selected sample in a position for subsequent processing.

BACKGROUND OF THE INVENTION

In complex manufacturing processes, it is frequently necessary to monitor the chemical, mechanical, metallurgical or other characteristics during the process. In particular, chemical composition manufacturing processes monitored by x-ray spectroscopy require the sampled material to be positioned to reflect or refract a beam of x-ray to a measuring detector, wherein position deviations by a few parts of a mil cause significant variations in analysis readings.

In a typical sample changer, samples, comprising rectangular samples of compressed material approximately 3×4 cm., are arranged in a linearly spaced tray of approximately 35 cm. in length and are retained within the sample tray by forces provided by spring elements. The sample tray is received by and moveable in a generally u-shaped channel piece of approximately twice the length of the sample tray, at about the center of which is a mechanism for which mechanically forces a selected sample through the bottom of the tray into a position defined on one surface by fixed, rigid members, and retained by spring members. The positioning and sample retaining spring members become fatigued and deformed over time and use, causing the apparatus to jam or otherwise improperly function. Furthermore, the spring retention typically used is relatively intolerant of accumulated residual particulate matter from the samples, causing wearing or displacement of the samples from the desired position. Moreover, so critical is the position of the sample x-ray spectroscopy that s significant sample displacement is dependent on the position of the sample tray within its channel. In particular, when the bulk of the sample tray is at either extreme, that is forward or rearward, sufficient bending of the support mechanism causes a variation in the x-ray spectroscopy reading of the sample.

Moreover, prior art sample changers have required the operator to place the samples in a particular sequence and in order, making it virtually difficult or inconvenient to operate or to attempt to adjust the weight of the sample tray by positioning the samples therein. Thus, the existing changers provide marginal reliability and problematic operation.

SUMMARY OF INVENTION

The apparatus according to the present invention positions sample substantially planar slides selected from a removable annular sample cassette wherein the samples are retained within the cassette positioned without spring members wherein the samples are permitted to slide freely from the cassette into the sample testing position and are retained therein by precisely positioned adjustable guide members and mechanical actuators. Additionally, the apparatus detects and agitates the mechanism to secure release of samples which become bound within the structure due to mechanical wear of the sample holders and or build up of sample particulate matter.

Additionally, the slides are generally retained in the annular cassette, during cassette transport by a concentric locking ring disposed on the outer periphery of one of the cassette mechanism. When in the locked position, all samples are retained within the cassette regardless of position of the cassette. When in the unlocked position, the samples are free to move radially outward from the cassette. When the cassette is inserted in the positioning mechanism, the cassette is perpendicular, permitting the samples to fall downward into a retaining portion of the positioning mechanism, having an aperture wherein a single position directly beneath the center of the cassette aligns with the aperture, permitting a sample to be lowered into the testing position.

In addition, the apparatus provides position sensing elements which locates each sample present, providing a numeric sequence independent of their location within the cassette holder, noting the number of samples and the location therein, obviating the need to have samples located in consecutive cassette location or position, the present apparatus provides a reliable trouble free sample selection and sample positioning for testing requiring minimal operator intervention and distribution of samples in the sample cassette, and wherein a reliable placement of the selected sample is provided.

BRIEF DESCRIPTION OF THE DRAWING

These and further features of the present invention will be better understood by reading the following detailed description, taken together with the drawing wherein:

FIG. 3 is a cross-section of the sample holder elevating and positioning elements of the embodiment of FIG. 3.

DETAILED DESCRIPTION OF THE INVENTION

Figure 1:
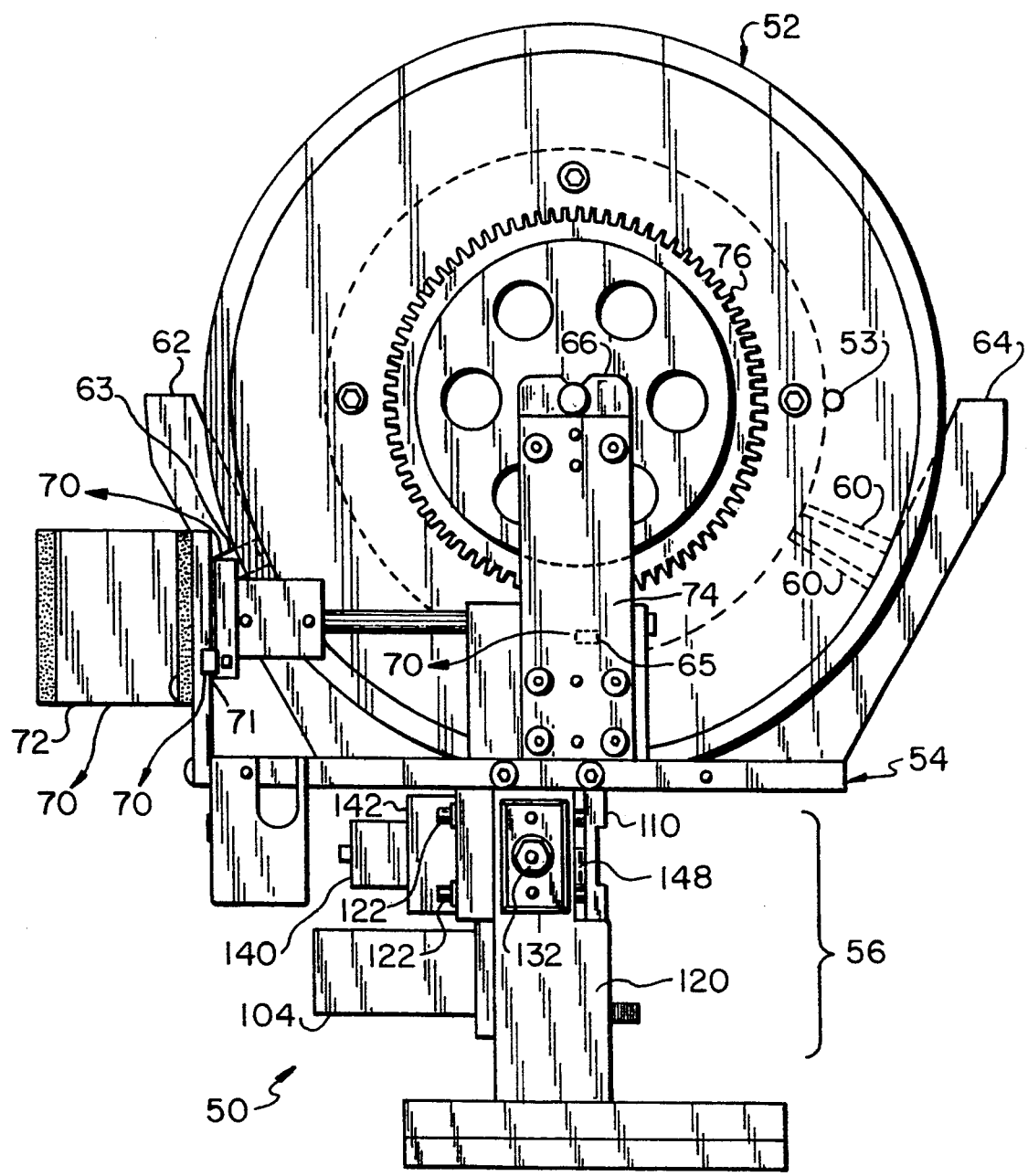
FIG. 1 is a side elevation view of one embodiment of the present invention.

The sample changer 50 according to one embodiment of the present invention is shown in FIG. 1 and comprises an annular sample cassette 52 which is retained in a support 54 disposed on a changer mechanism 56 which positions the selected sample for testing. A plurality of slides 60 (shown in phantom) are radially disposed within the annular cassette 52 which when unlocked, are permitted to fall downward away from the center of the cassette 52 in response to the pull of gravity. Retaining guide members 62 and 64 form a semicircular guide element which retains the samples within the cassette 52. The guides 62 and 64 have an aperture therebetween at the portion of the circumference corresponding to the lowest location of the cassette 52, through which aperture (not shown) the released sample is lowered by elements of the mechanism 56.

Figure 3A:
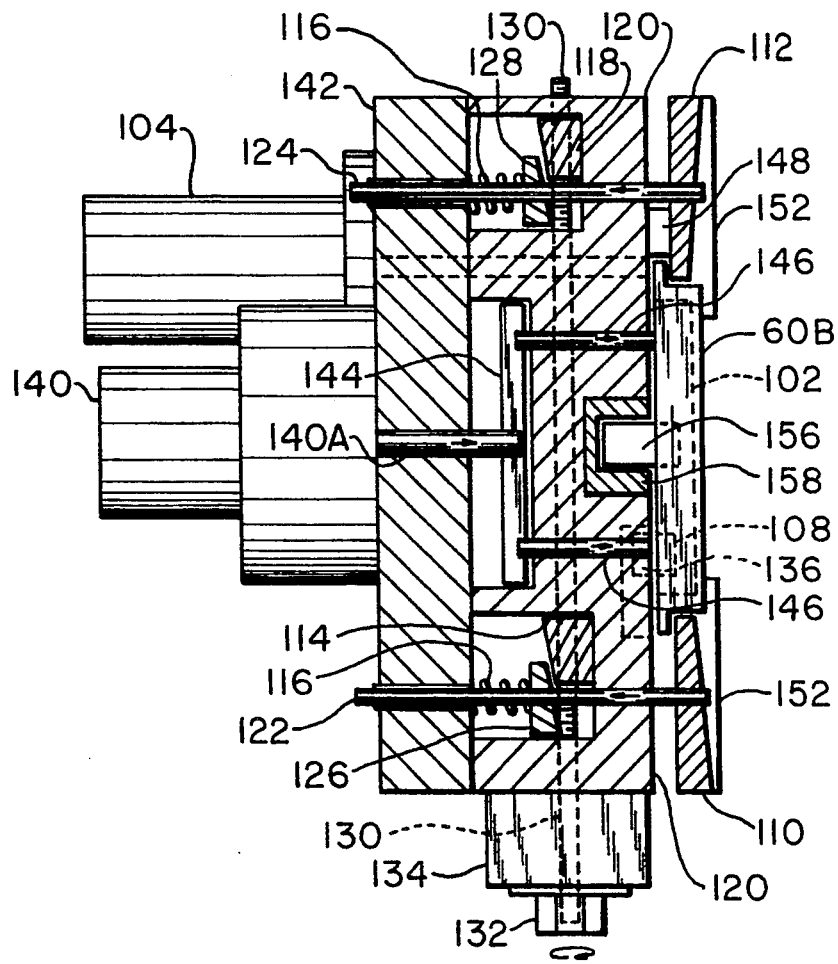
FIG. 3 is an exploded view of the sample holder elevating and positioning elements according to the embodiment shown in FIG. 1.
Figure 3:
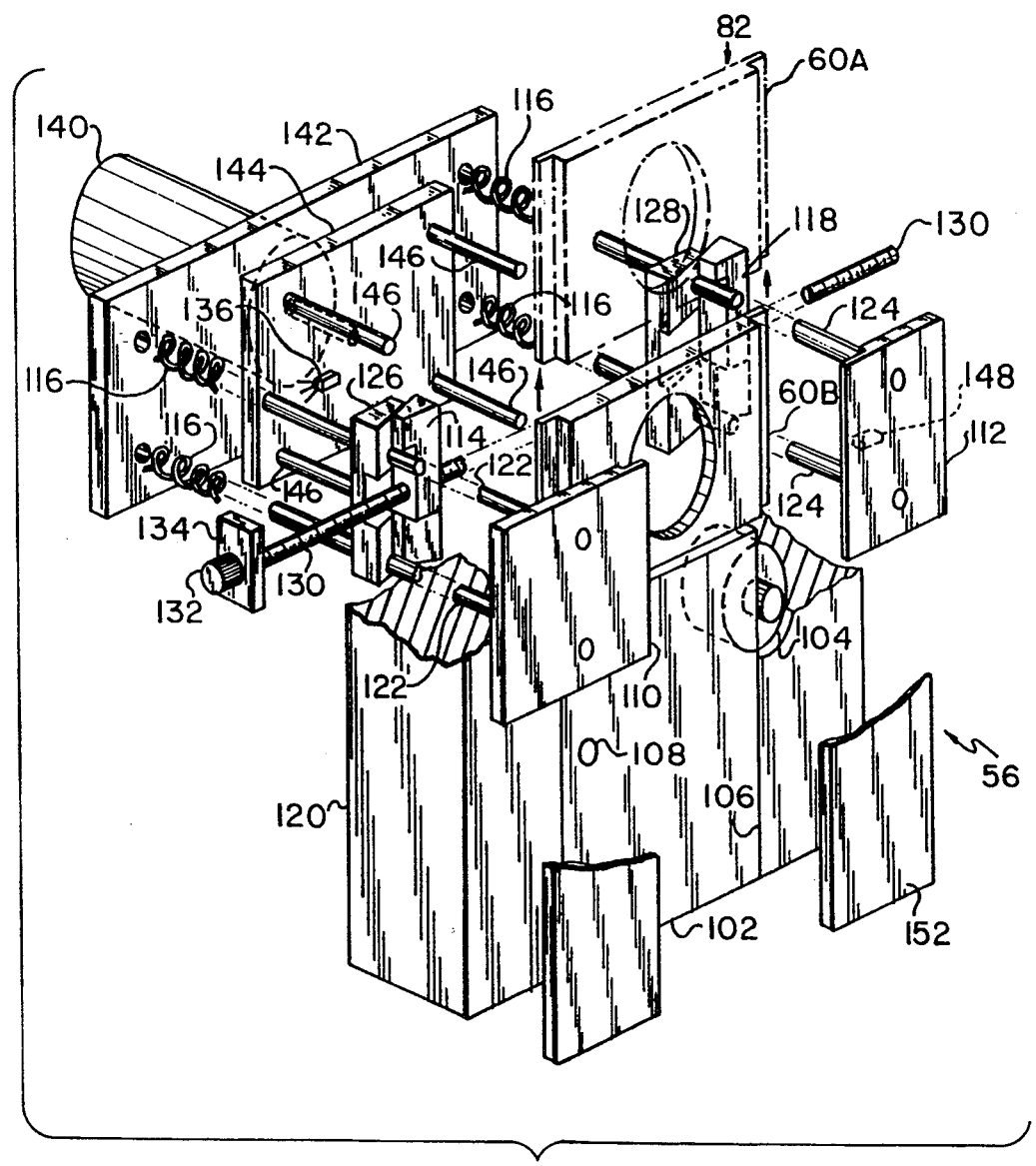

Positioning mechanism 56 is shown in greater detail in FIGS. 3 and 3A wherein the slide 60 in the raised position shown as 60A is lowered into the testing position 60B by the vertically moving member 102 actuated by drive motor 104 having a gear to engage the teeth on 106 on the vertical edge member 102. Accordingly the selected sample 60 is lowered into position by lowering the member 102 wherein the sample 60 follows the member 102 by gravity. The main support 120 retains the sliding member 102 and includes therein recesses for further mechanism 56 structures.

Figure 2:
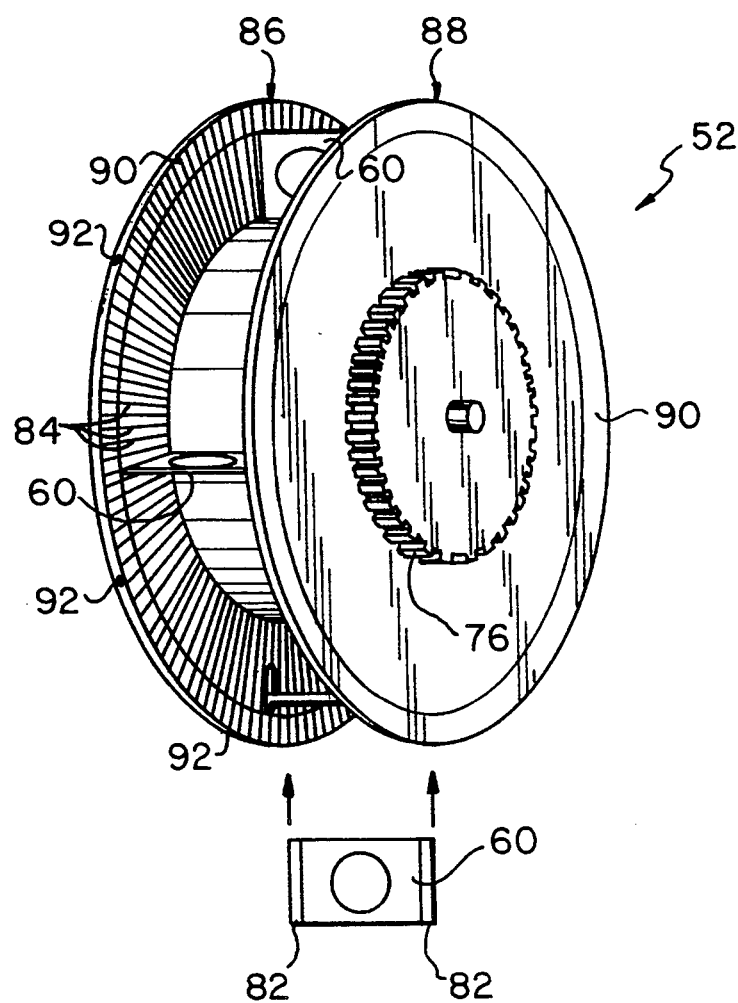
FIG. 2 is a perspective drawing of the annular sample holder according to one embodiment of the present invention.

The annular cassette 52 is shown in more detail in FIG. 2 wherein samples 60 are retained in various radial positions within the annular sample cassette 52. In particular, the sample holders, typically having reduced thickness edges 82 are received in slots 84 provided in the side members 86 and 88 of the annular sample cassette 52. The samples are freely moveable within the slots 84, and are held therein by a concentric locking ring 90 which is partially rotatable about the axis of the sample cassette 52 as discussed in further detail in FIG. 2A.

Figure 2A:
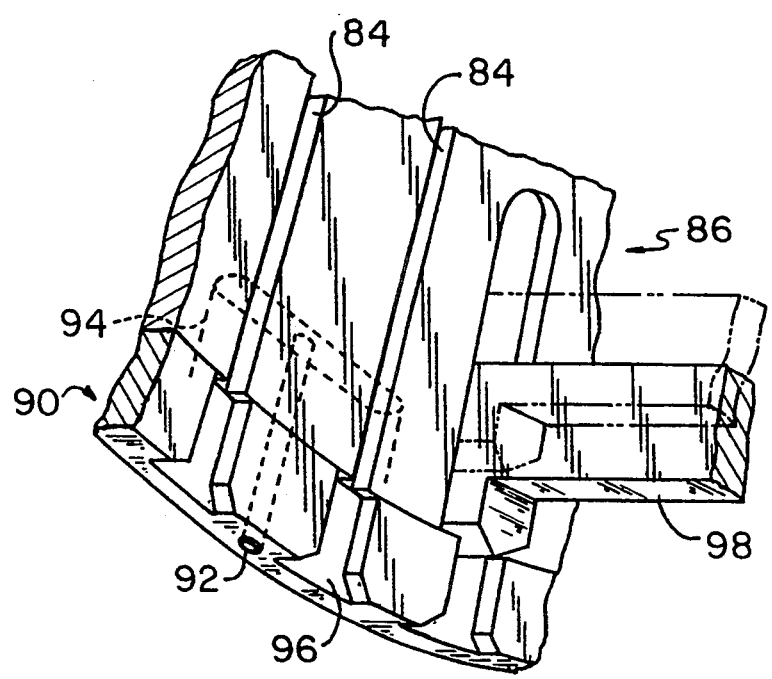
FIG. 2A is an enlargement of the sample holder shown in FIG. 2.

In FIG. 2A the side member 86 is shown having a concentric sample locking ring 92 affixed thereabouts by a plurality of radially disposed pins 90 2 which extend through the locking ring 90 and into a corresponding recesses 94 provided at the periphery of the side member 86 at periodic angular intervals. When the pin 92 is centered within the recess 94, the slots 96 are aligned with side member slots 84 permitting removal of the samples 60. The locking ring 90 is held in the unlocked position by radially outward movement of a locking key 98 which serves to align locking ring slots 96 with the side member 84. When the locking key 98 is retracted towards the axis of the sample cassette, the locking ring is rotated to occlude the end of the slots 84, thereby retaining the samples within the sample cassette 52.

The forward position of the sample when lowered, 60B, is provided by retainers 110 and 112 shown in FIG. 3 and FIG. 3A, which retainers are adjusted according to a pair of sliding inclined surfaces wherein each retainer 110, 112 is connected to a sliding member 114, 118 by rods 122 and 124 which pass through the body of the support 120. The inclined members 114 and 118 are threaded to receive screw 130, moving laterally with respect to the support 120 according to the rotation of screw 130 which is operated by nut 132 against a plate 134 affixed to the main support 120. The opposite surface of each of the inclined members 114 and 118 contact inclined members 126 and 128 which are rigidly connected to the retainers 110 and 112 by connecting rods 122 and 124 respectively. The inclined members 126, 128 and thus also retainers 110 and 112 are urged forward by spring elements 116 which are concentrically disposed about the rods 122 and 124, having their opposite end against a solenoid mounting plate 142 which is rigidly affixed to the main support 120. Thus when assembled, the retainer element 110 and 112 are urged forward, away from the support 120 except as displaced rearward by inclined members 114 and 118, which acts against the force provided by spring elements 116 according to rotation of the screw 130 which causes the inclined members 114 and 118 to move laterally with respect to the body 120 upon rotation of the nut 132, thereby securing an accurate and repeatable forward location of the sample 60B in the sample position. When the sample such as sample 60A is raised into the sample cassette 52 the raised condition of a vertically sliding member 102 is detected by the juxtaposition of magnet 108 by the Hall effect device 136. When lowered into the testing position, sample 60B is detected by optical sensor 148 located behind retaining element 112 in a recess (not shown) in support 120. In the sample testing position 60B, the sample is retained accurately against the retainer 110 and 112 by solenoid 140 which provides a force on the sample 60B through shaft 140A, a force distribution plate 144 and four separate rods 146 having equal length and disposed through a support 120 to provide substantially uniform pressure against the rear side of sample 60B to firmly and accurately seat sample against the retainer 110 and 112.

Figure 1A:
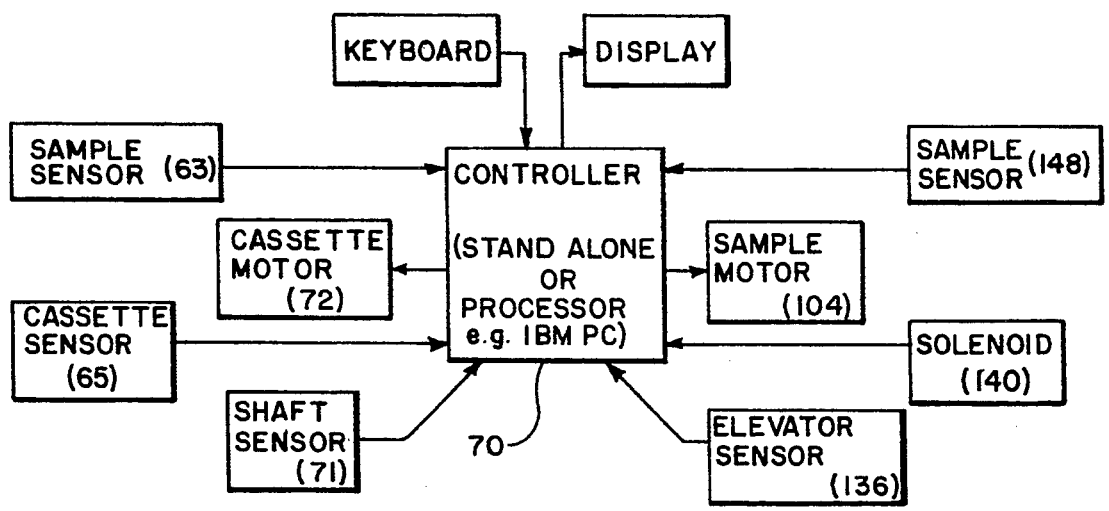
FIG. 1A is a block diagram showing the interconnection of the control, actuation and sensor elements of one embodiment of the present invention.

In operation, the sample cassette 52 is seated in the sample support 66 and is rotationally driven thereabout by a drive motor 72 via worm gear 74 and ring gear 76 attached to the sample cassette 52. When operation is initiated, the motor 72 rotates the cassette through at least one complete revolution while the controller 70 counts the samples 60 detected by the optical sensor 63 as the cassette 52 is rotated. The absolute and relative position of the samples and sample vacancies within the cassette 52 is determined by the rotation of the motor 72 (determined according to sensor 71) and the detection of the position of the cassette within the sample changer 54 by detection of a reference position by the magnet 53 affixed to side member of cassette 52 by the sensor 65 connected to the cassette support 66, and the relative number of motor 72 shaft rotations as detected by sensor 71. Upon completion of a complete count of the sample 60 within the cassette 52 by at least a complete rotation of the cassette 52 by motor 72, the samples are numbered by controller (70, FIG. 1A), omitting vacant spaces in the cassette 52 in the number sequence, the operator may selectively test a selected sample 62 in the numeric sequence in which they occur independent of the exact position within the wheel. Specifically, the empty spaces are ignored, and the samples may be distributed as desired without concern of unbalancing the structure and thus affecting the position of the sample when in the testing position.

To select the sample to be placed in the test position, the sample cassette 52 is rotated so as to position the selected sample in the lowest, vertical position of the cassette to coincide with the aperture 61 between the guide element 62 and 64. Thereupon, gravity will cause the sample 62 to be lowered downward upon actuation of motor 104 which lowers the vertical moving member 102 downward into the structure support 120. The sample is precisely positioned by the rotation of screw 130, relatively moving the confronting incline member pairs 114, 126 and 118, 128 which accurately move retainers 110 and 112, providing the desired precise positioning of the sample 60B. Thereafter, the sample is retained against the retainers 110 and 112 by application of a force by solenoid 140 (via shaft 140A, FIG. 3A).

In the event that a sample is jammed within the structure, the failure of the various elements to move into their respective positions is detected by the aforementioned sensors (136, 65, 63, and 71,) wherein the controller causes the respective related elements to be pulsed at a rate between 1 and 10 pulses per second to dislodge the elements and permit resumed motion thereof. For instance, were the sample 60B to be unable to be raised into the cassette, the sensor 136 would fail to detect the presence of magnet 108 or that sensor 148 detected the continued presence of sample 60B, indicating that the sample 60B was jammed or that vertical elevating member 102 was inoperable, wherein the motor 104 would be pulsed at the aforementioned pulse rate to dislodge the sample 60B. Similarly, the solenoid 140 is then pulsed or repetitively actuated to cause the sample 60B to become dislodged and normal operations resumed.

The cross-section of the assembled sample elevating and positioning structure is shown in FIG. 3A. In addition to further illustrating some of the elements of FIG. 3, cover members 152 for partially covering and retaining the vertically moving member 102. is shown. The vertically moving member 102 are guided by pin 156 in channel 158. Several elements (112, 114, 122, 124, 140A, 146) show the application of force on seated sample 60A with arrows (e.g.→) resulting from the rotation of nut 132 or actuation of the solenoid 140.

Thus, the apparatus provides precise positioning of samples in a hostile environment wherein operator intervention is minimized and techniques are applied to maintain reliable operation in the event of temporary failure. Moreover, the terms used to define the particular embodiment shown are not limiting, and may be construed to also describe apparatus of other orientations, such as illustrated by the term "forward" which may also be understood to mean to the side or rear according to corresponding variations in implementation. Thus, modifications and substitutions made by one of ordinary skill in the art are considered within the scope of the present invention, which is not to be limited except by the claims which follows.

What is claimed is:

1. An annular cassette for receiving a plurality of standardized objects, comprising:

substantially parallel annular planar members having positions provided thereon radially disposed from an axis, for receiving opposite edge portions of said standardized objects;

a locking ring disposed on one of said annular planar members and rotatable relative thereto having a first position for retaining said standardized objects within said cassette and a second position releasing at least a plurality of said standardized objects.

2. The annular cassette of claim 1, wherein said planar members include a plurality of uniformly spaced radially disposed slots therein providing said positions for receiving said standardized objects.

3. The annular cassette of claim 1 further including a locking key retained between said annular planar members, for engaging said locking ring in said first and second position.

4. The annular cassette of claim 1, wherein said locking ring includes a plurality of pins extending radially into elongated recesses at the periphery of said annular planar member, said pins being uniformly spaced about the locking ring, wherein said locking ring is movable according to the edge length of said elongated recesses.

* * * * *